United States Patent
Wang et al.

(10) Patent No.: US 9,365,505 B2
(45) Date of Patent: Jun. 14, 2016

(54) PHOTORESIST MONOMER, PHOTORESIST AND METHOD FOR THE PREPARATION THEREOF, COLOR FILTER

(71) Applicant: BOE TECHNOLOGY GROUP CO., LTD., Beijing (CN)

(72) Inventors: Xuelan Wang, Beijing (CN); Chen Tang, Beijing (CN)

(73) Assignee: BOE TECHNOLOGY GROUP CO., LTD, Beijing (CN)

( * ) Notice: Subject to any disclaimer, the term of this patent is extended or adjusted under 35 U.S.C. 154(b) by 15 days.

(21) Appl. No.: 14/381,746

(22) PCT Filed: Dec. 13, 2013

(86) PCT No.: PCT/CN2013/089332
§ 371 (c)(1),
(2) Date: Aug. 28, 2014

(87) PCT Pub. No.: WO2015/007049
PCT Pub. Date: Jan. 22, 2015

(65) Prior Publication Data
US 2016/0009641 A1  Jan. 14, 2016

(30) Foreign Application Priority Data
Jul. 15, 2013  (CN) .......................... 2013 1 0302391

(51) Int. Cl.
| | |
|---|---|
| G03F 7/027 | (2006.01) |
| G03F 7/031 | (2006.01) |
| G02B 5/20 | (2006.01) |
| C07C 309/73 | (2006.01) |
| G03F 7/00 | (2006.01) |
| G03F 7/004 | (2006.01) |
| C07C 303/26 | (2006.01) |
| G02B 5/22 | (2006.01) |

(52) U.S. Cl.
CPC ............ *C07C 309/73* (2013.01); *C07C 303/26* (2013.01); *G02B 5/201* (2013.01); *G02B 5/223* (2013.01); *G03F 7/004* (2013.01); *G03F 7/0007* (2013.01); *G03F 7/027* (2013.01); *G03F 7/031* (2013.01)

(58) Field of Classification Search
CPC ....... G03F 7/0007; G03F 7/031; G03F 7/027; G02B 5/201; G02B 5/223; C07C 309/73; C07C 303/26
USPC .............................. 430/7, 281.1, 286.1, 288.1
See application file for complete search history.

(56) References Cited

U.S. PATENT DOCUMENTS

| | | | |
|---|---|---|---|
| 6,114,085 A | 9/2000 | Padmanaban et al. | |
| 6,956,091 B2 | 10/2005 | Hong et al. | |
| 8,252,879 B2 | 8/2012 | Kim et al. | |
| 8,357,483 B2 | 1/2013 | Kim et al. | |
| 2008/0241713 A1* | 10/2008 | Tanaka .................... | G03F 7/027 430/7 |

FOREIGN PATENT DOCUMENTS

| | | |
|---|---|---|
| CN | 1330779 A | 1/2002 |
| CN | 1699436 A | 11/2005 |
| CN | 101641642 A | 2/2010 |
| CN | 101652713 A | 2/2010 |
| CN | 103351465 A | 10/2013 |
| WO | 2015007049 A1 | 1/2015 |

OTHER PUBLICATIONS

English Translation of the International Search Report of PCT/CN2013/089332 published in English on Jan. 22, 2015.
Written Opinion of the International Searching Authority of PCT/CN2013/089332 in English, mailed Apr. 23, 2014.
International Search Report of the International Searching Authority of PCT/CN2013/089332 in English, mailed Apr. 23, 2014.
International Search Report, International Preliminary Report on Patentability and Written Opinion of the International Searching Authority of PCT/CN2013/089332 in Chinese, mailed Apr. 23, 2014.

* cited by examiner

Primary Examiner — John A McPherson
(74) Attorney, Agent, or Firm — Collard & Roe, P.C.

(57) ABSTRACT

A photoresist monomer, a photoresist and a method for the preparation thereof, a color filter. The photoresist monomer has a structure represented by Formula I,

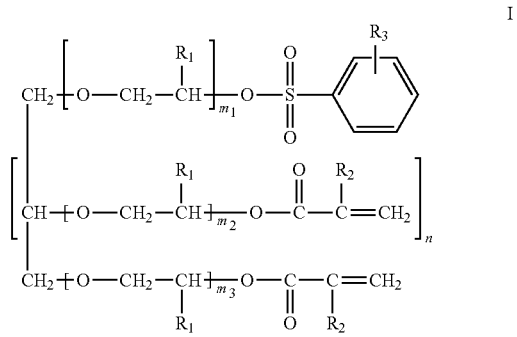

wherein, $R_1$ is hydrogen or methyl; $R_2$ is hydrogen, methyl, ethyl, or propyl; $R_3$ is hydrogen or $C_{1-6}$ alkyl; and n is from 1 to 4. The resulting photoresist exhibits a compact and smooth surface and a gentle angle of slope.

14 Claims, 3 Drawing Sheets

PHOTORESIST MONOMER, PHOTORESIST AND METHOD FOR THE PREPARATION THEREOF, COLOR FILTER

CROSS REFERENCE TO RELATED APPLICATIONS

This application is the National Stage of PCT/CN2013/089332 filed on Dec. 13, 2013, which claims priority under 35 U.S.C. §119 of Chinese Application No. 201310302391.8 filed on Jul. 15, 2013, the disclosure of which is incorporated by reference.

TECHNICAL FIELD

Embodiments of the invention relate to a photoresist monomer, a photoresist and a method for the preparation thereof, a color filter.

BACKGROUND

A color filter is a key component for a liquid crystal display to enable colorizing. The process for preparing a color filter comprises forming a black matrix on a substrate, coating a photoresist onto the substrate having the black matrix formed thereon, and subjecting the photoresist to pre-baking, masking, and exposure, whereby the exposed photoresist will undergo a cross-linking reaction such that it is remained in a subsequent alkaline developing process, and the remained pattern will be cleansed, developed and hard-baked at a high temperature, to produce the color filter.

During the process of producing the black matrix and the filter layer, the edge portion of the filter layer connects to the black matrix at a certain gradient to avoid light leak. Because most of the photoresists exhibit a high rigidity after high-temperature hard baking, the resulting filter layer is not liable to bend and sink to form a gradient. This results in a steep angle of slope occurring in the connections between the black matrix and the filter layer, which would easily cause light leak. The embodiments of the present invention aim to provide a photoresist having a compact and smooth surface and a gradual angle of slope.

SUMMARY

An embodiment of the present invention provides a photoresist monomer having a structure represented by Formula I, wherein, $R_1$ is hydrogen or methyl; $R_2$ is hydrogen, methyl, ethyl, or propyl; $R_3$ is hydrogen or $C_{1-6}$ alkyl; and n is from 1 to 4.

In Formula I, $m_1$, $m_2$, and $m_3$ are in the range of 50-400.

An embodiment of the present invention provides a photoresist comprising the aforesaid photoresist monomer or a mixture of photoresist monomers.

Said photoresist further comprises an alkaline soluble resin, a pigment dispersion, a photoinitiator, a solvent, and an adjuvant; said photoresist comprising, in part by weight, photoresist monomer or a mixture of photoresist monomers: 11.2-21.2 parts;
alkaline soluble resin: 7.4-19.8 parts;
pigment dispersion: 35.2-57.6 parts;
photoinitiator: 1.8-11.9 parts;
solvent: 11.26-28.5 parts; and
adjuvant: 0.07-0.21 part.

For example, the mixture of the photoresist monomers comprises photoresist monomers A, B, and C, wherein,
the photoresist monomer A has a structure of Formula I in which n is 1, and is in 1 part by weight;
the photoresist monomer B has a structure of Formula I in which n is 2, and is in 2.3-4.3 parts by weight; and
the photoresist monomer C has a structure of Formula I in which n is 3, and is in 5.1-5.7 parts by weight.

For example, the mixture of the photoresist monomers comprises photoresist monomers A, B, and D, wherein,
the photoresist monomer A has a structure of Formula I in which n is 1, and is in 1 part by weight;
the photoresist monomer B has a structure of Formula I in which n is 2, and is in 2.7-3.5 parts by weight; and
the photoresist monomer D has a structure of Formula I in which n is 4, and is in 3.3-5.5 parts by weight.

For example, the mixture of the photoresist monomers comprises photoresist monomers B, C, and D, wherein,
the photoresist monomer B has a structure of Formula I in which n is 2, and is in 1 part by weight;
the photoresist monomer C has a structure of Formula I in which n is 3, and is in 2.3-3.1 parts by weight; and
the photoresist monomer D has a structure of Formula I in which n is 4, and is in 4.7-7.5 parts by weight.

An embodiment of the present invention provides a color filter, comprising:
a substrate;
a black matrix provided on the substrate; and
a color filter lap-jointly provided on the black matrix, said color filter being formed by the photoresist according to the embodiment of the present invention.

In another embodiment of the present invention, a method for preparing the photoresist monomer is provided, which comprises:

(1) reacting polyether polyol as shown by Formula II with $R_3$-substituted benzenesulfonyl chloride as shown by Formula III

III in a proper solvent, to generate $R_3$-substituted benzenesulfonyl chloride-modified polyether polyol as shown by Formula IV;

IV (2) reacting $R_3$-substituted benzenesulfonyl chloride-modified polyether polyol as shown by Formula IV with $R_2$-substituted acryloyl chloride as shown by Formula V

V in a proper solvent in the presence of a catalyst, to generate the photoresist monomer of Formula I, wherein, $R_1$, $R_2$, $R_3$, n, $M_1$, $m_2$, and $m_3$ are defined as above.

In the above method, polyether polyol, $R_3$-substituted benzenesulfonyl chloride, and the solvent in step (1) are, in parts by weight:

polyether polyol: 2 parts;
$R_3$-substituted benzenesulfonyl chloride: 0.7-0.9 part;
solvent: 100-160 parts.

In the above method, $R_3$-substituted benzenesulfonyl chloride-modified polyether polyol, $R_2$-substituted acryloyl chloride, the solvent, and the catalyst in step (2) are, in parts by weight:

$R_3$-substituted benzenesulfonyl chloride-modified polyether polyol: 1 part;
$R_2$-substituted acryloyl chloride: 2.3-6.1 parts;
solvent: 45-135 parts;
catalyst: 0.015-0.035 part.

An embodiment of the present invention further provides a method for preparing the photoresist, comprising:

Step Q1: mixing a photoinitiator, a solvent, and an adjuvant with stirring, until the photoinitiator is dissolved;

Step Q2: adding a mixture of an alkaline soluble resin, and a photoresist monomer or a mixture thereof to the mixed solution from step Q1, and stirring the mixture to a transparent state;

Step Q3: adding a pigment dispersion to the mixture from step Q2, to produce the photoresist.

BRIEF DESCRIPTION OF THE DRAWINGS

The Figures useful for the embodiments will be simply described in order to illustrate the embodiments of the present invention or the prior art more clearly. It is obvious that the described Figures represent only a portion of the embodiments of the present invention. Based on these Figures, persons of ordinary skill in the art can obtain other figures without creative work.

DETAILED DESCRIPTION

In order to make objects, technical details and advantages of the embodiments of the invention apparent, the technical solutions of the embodiment will be described in a clearly and fully understandable way in connection with the drawings related to the embodiments of the invention. It is obvious that the described embodiments are just a part but not all of the embodiments of the invention. Based on the described embodiments herein, those skilled in the art can obtain other embodiment(s), without any inventive work, which should be within the scope of the invention.

The photoresist monomer, the photoresist and the method for preparing thereof as well as the color filter according to embodiments of the present invention will be described in a clearly and fully understandable way in connection with the drawings.

An embodiment of the present invention provides a photoresist monomer having a structure represented by Formula I.

I wherein, $R_1$ is hydrogen or methyl; $R_2$ is hydrogen, methyl, ethyl, or propyl; $R_3$ is hydrogen or $C_{1-6}$ alkyl, for example, $R_3$ is hydrogen or $C_{1-6}$ alkyl (preferably, methyl, ethyl, or isopropyl) substituted on a para-position, for example, $R_3$ is hydrogen, methyl, ethyl, or propyl; and n is from 1 to 4, preferably, n is 2, 3, or 4.

In the polyether chain of the embodiment, $m_1$, $m_2$, and $m_3$ are in the range of 50-400. For example, the photoresist monomer has a molecular weight of less than 18000.

The embodiments of the present invention provide a photoresist monomer, a photoresist and a method for preparing thereof as well as a color filter. Said photoresist monomer is generated by a reaction of $R_3$-substituted benzenesulfonyl chloride-modified polyether polyol with $R_2$-substituted acryloyl chloride. The $R_2$-substituted acryloyl structure has a double-bond functional group. When used in the photoresist, the photoresist monomer will form a compact network through the self-crosslinking of the double-bond groups or the cross-linking of the double-bond groups with other components in the photoresist, such that the resulting film exhibits a compact and smooth surface upon high temperature post-baking. The $R_3$-substituted benzenesulfonyl group contains an aromatic group which can increase the compatibility of the monomer with the pigment or other components present in the photoresist system and enhance the film-forming ability of the polyether chain. The $R_3$-substituted benzenesulfonyl group has an excellent heat resistance and the incorporation of a sulfonyl group into polyether polyol can increase the solubility in the polar solvent and high-temperature heat resistance of polyether polyol. $R_3$-substituted benzenesulfonyl chloride-modified polyether polyol has good flexibility, low melting point, good solubility and heat resistance. Use of $R_3$-substituted benzenesulfonyl chloride-modified polyether polyol avoids the photoresist monomer to have high rigidity after baking at a high temperature, increases the gentle degree of angle of slope between film layers, avoids light leak caused by an uneven coating of a PI alignment film during the subsequent process, and improves the performance of the photoresist.

An embodiment of the present invention provides a photoresist comprising the photoresist monomer according to the aforesaid embodiment or a mixture thereof.

The mixture of the photoresist monomers varies depending on the length of the polyether chain, the number of n, and the substituents $R_1$, $R_2$, and $R_3$ in the photoresist monomers. Here, if the length of the polyether chain is too short, the film formed after the curing of the photoresist is quite rigid and fragile. If the length of the polyether chain is too long, the film formed after the curing of the photoresist has low mechanical strength and poor rigidity and flexibility. Preferably, each of $m_1$, $m_2$, and $m_3$ in the polyether chain in the embodiments of the present invention can be in a range of 50-400.

Further, the value of n directly reflects the number of the double bonds present in the $R_2$-substituted acryloyl functional group. According to the number of the double bonds, the photoresist monomer can be classified into a low-functionality monomer and a high-functionality monomer. Here, the high-functionality monomer has a rapid photo-curing rate and a high cross-liking density and the cured product is quite rigid. On the contrary, the low-functionality monomer has a slow photo-curing rate and a low cross-liking density and the cured product is relatively flexible and easy to produce.

The photoresist monomer according to the embodiment of the present invention has a $R_2$-substituted acryloyl structure which contains a double-bond functional group in its structure. When used in the photoresist, the photoresist monomer will form a compact network through the self-crosslinking of the double-bond group or the cross-linking of the double-bond group with other components in the photoresist, such that the resulting film exhibits a compact and smooth surface upon high temperature post-baking. Further, the $R_3$-substituted benzenesulfonyl group contains an aromatic group which can increase the compatibility of the monomer with the pigment or other components present in the photoresist system and enhance the film-forming ability of the polyether chain. The $R_3$-substituted benzenesulfonyl group has an excellent heat resistance and the incorporation of a sulfonyl group into polyether polyol can increase the solubility in the polar solvent and high-temperature heat resistance of polyether polyol. $R_3$-substituted benzenesulfonyl chloride-modified polyether polyol has good flexibility, low melting point, good solubility and heat resistance. Use of $R_3$-substituted benzenesulfonyl chloride-modified polyether polyol avoids the photoresist monomer to have high rigidity after baking at a high temperature, increases the gentle degree of angle of slope between film layers, avoids light leak caused by an uneven coating of a PI alignment film during the subsequent process, and improves the performance of the photoresist.

The embodiment of the present invention further provides a formulation of a photoresist, comprising a alkaline soluble resin, a pigment dispersion, a photoinitiator, a solvent, and an adjuvant; said photoresist comprising, in part by weight, photoresist monomer or a mixture of the photoresist monomers: 11.2-21.2 parts; alkaline soluble resin: 7.4-19.8 parts; pigment dispersion: 35.2-57.6 parts; photoinitiator: 1.8-11.9 parts; solvent: 11.26-28.5 parts; and adjuvant: 0.07-0.21 parts.

In the formulation, the alkaline soluble resin can be alkaline soluble acrylic soluble resin, such as, polymethacrylate or amine-modified acrylate. The pigment dispersions are not limited to specific colors, and can be any suitable types depending on the photoresist actually formulated, which can be one or more of red pigments, green pigments, yellow pigments, blue pigments, violet pigments, cyan pigments, and black pigments. The photoinitiator can be selected from one or more of benzoins, benzophenones, and anthraquinones. The solvent can be selected from one or more of propylene glycol monomethyl ether acetate, propylene glycol diacetate, ethyl 3-ethoxy-3-iminopropionate, 2-methyl-heptane, 3 methyl-heptane, cyclopentanone, and cyclohexanone. The adjuvant can be selected from one or more of a silane coupling agent, an antioxidant, an UV absorber, an antifoaming agent, and a leveling agent. These materials are well known in the art for preparing a photoresist composition and persons skilled in the art will easily select a specific type upon reading the present description.

The embodiment of the present invention further provides a formulation of a photoresist, to which the photoresist monomer or a mixture thereof is added. The photoresist monomer has a $R_2$-substituted acryloyl structure which contains a double-bond functional group in its structure. When used in the photoresist, the photoresist monomer will form a compact network through the self-crosslinking of the double-bond group or the cross-linking of the double-bond group with other components in the photoresist, such that the resulting film exhibits a compact and smooth surface upon high temperature post-baking. Further, the $R_3$-substituted benzenesulfonyl group contains an aromatic group which can increase the compatibility of the monomer with the pigment or other components present in the photoresist system and enhance the film-forming ability of the polyether chain. The $R_3$-substituted benzenesulfonyl group has an excellent heat resistance and the incorporation of a sulfonyl group into polyether polyol can increase the solubility in the polar solvent and high-temperature heat resistance of polyether polyol. $R_3$-substituted benzenesulfonyl chloride-modified polyether polyol has good flexibility, low melting point, good solubility and heat resistance. Use of $R_3$-substituted benzenesulfonyl chloride-modified polyether polyol avoids the photoresist monomer to have high rigidity after baking at a high temperature, increases the gentle degree of angle of slope between film layers, avoids light leak caused by an uneven coating of a PI alignment film during the subsequent process, and improves the performance of the photoresist.

In another embodiment, a mixture of the photoresist monomers can be introduced into the photoresist, said the photoresist monomers having a structure of formula I:

the mixture of the photoresist monomers can comprise photoresist monomers A, B, and C, wherein, the photoresist monomer A has a structure of Formula I in which n is 1 and is in 1 part by weight; the photoresist monomer B has a structure of Formula I in which n is 2 and is in 2.3-4.3 parts by weight; and the photoresist monomer C has a structure of Formula I in which n is 3 and is in 5.1-5.7 parts by weight. Alternatively, the mixture of the photoresist monomers can comprise photoresist monomers A, B, and D, wherein, the photoresist monomer A has a structure of Formula I in which n is 1 and is in 1 part by weight; the photoresist monomer B has a structure of Formula I in which n is 2 and is in 2.7-3.5 parts by weight; and the photoresist monomer D has a structure of Formula I in which n is 4 and is in 3.3-5.5 parts by weight. Alternatively, the mixture of the photoresist monomers can comprise photoresist monomers B, C, and D, wherein, the photoresist monomer B has a structure of Formula I in which n is 2 and is in 1 part by weight; the photoresist monomer C has a structure of Formula I in which n is 3 and is in 2.3-3.1 parts by weight; and the photoresist monomer D has a structure of Formula I in which n is 4 and is in 4.7-7.5 parts by weight.

An embodiment of the present invention provides a scheme for formulating a photoresist. In the scheme, the photoresist used are produced by mixing photoresist monomers having different functionality in a certain proportion. In such scheme for formulating the photoresist, the amounts of the monomers having different functionality should be in a proper proportion. If the amount of low-functionality photoresist monomer used is too high, the peripheral network structure formed after exposing internal structure is insufficient in cross-linking degree, and the surface of the resulting cured film appears porous. If the amount of low-functionality photoresist monomer used is too low, after internal structure is exposed and cured, the photoresist monomers will be further subjected to self-crosslinking during the process of high temperature post-baking, resulting in a film which may be dense somewhere and thin otherwise, and have a surface being unsmooth and liable to contract.

Here, relatively, A and B can be called low-functionality photoresist monomers, and C and D can be called high-functionality photoresist monomers. In the embodiments of the present invention, a mixture consisting of photoresist monomers A, B, and C, a mixture consisting of photoresist monomers A, B, and D, and a mixture consisting of photoresist monomers B, C, and D are exemplified, respectively. By formulating the monomers having different functionality in a certain part by weight, it provides suitable functionality such that the cross-linking degree required for forming the peripheral network structure upon exposure could be satisfied, while avoiding further self-crosslinking occurring during the process of high temperature post-baking. Further, the formulation scheme provided by the embodiment of the present invention imparts a suitable photo-curing rate and flexibility of the cured product, such that the photoresist achieves an improvement in performance.

An embodiment of the present invention provides a color filter, comprising: a substrate; a black matrix provided on the substrate; and a color filter lap-jointly provided on the black matrix, said color filter being formed by the photoresist according to the embodiment of the present invention.

Because the color filter is coated with the photoresist, which is produced by mixing photoresist monomers prepared by a substitution reaction between $R_3$-substituted benzenesulfonyl chloride-modified polyether polyol and $R_2$-substituted acryloyl structure, the photoresist can, during the process of exposure, be well cross-linked in oneself or with other components in the photoresist composition via the double-bond group. Further due to the fact that the polyether structure has good compliance, low melting point, and good solubility, it will prevent the photoresist from having high rigidity when baking at a high temperature, increase the gentle degree of angle of slope between film layers, avoid light leak, and improve the performance of the photoresist.

Figure 1:
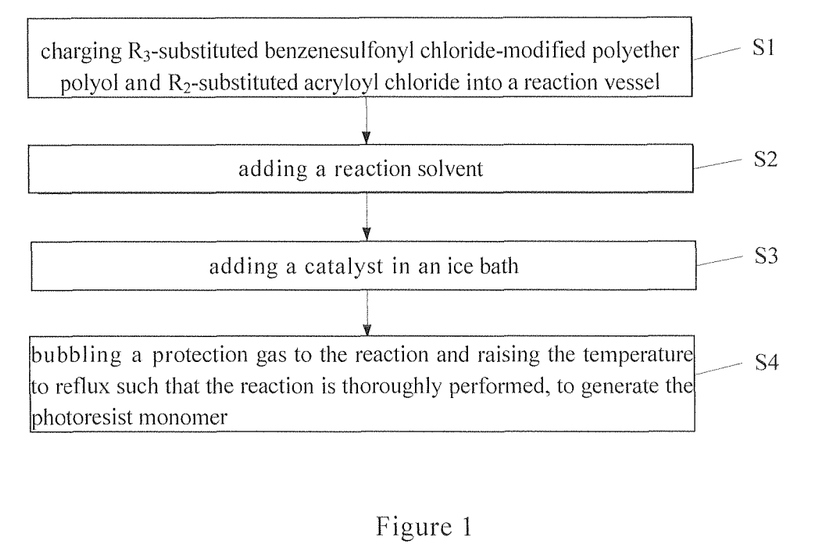
FIG. 1 is a process flow chart of preparing a photoresist monomer according to an embodiment of the present invention.

Corresponding to the photoresist monomer, the embodiment of the present invention further provides a method for preparing the photoresist monomer. As shown in FIG. 1, the method comprises:

Step S1: charging $R_3$-substituted benzenesulfonyl chloride-modified polyether polyol as shown by Formula IV and $R_2$-substituted acryloyl chloride as shown by Formula V into a reaction vessel, In this step, appropriate amounts of $R_3$-substituted benzenesulfonyl chloride-modified polyether polyol and $R_2$-substituted acryloyl chloride are weighted and added to a reaction vessel. For example, $R_3$-substituted benzenesulfonyl chloride-modified polyether polyol used in this step is 1 part by weight, and $R_2$-substituted acryloyl chloride used in this step is 2.3-6.1 parts by weight.

Step S2: adding a reaction solvent

In this step, appropriate reaction solvent is weighted. For example, the reaction solvent used in the step is 45-135 parts by weight, and $R_3$-substituted benzenesulfonyl chloride-modified polyether polyol used in this step is 1 part by weight.

Step S3: adding a catalyst in an ice bath

In this step, appropriate catalyst is weighted. For example, the catalyst used in the step is 0.015-0.035 part by weight, and $R_3$-substituted benzenesulfonyl chloride-modified polyether polyol used in this step is 1 part by weight.

Step S4: bubbling a protection gas to the reaction and raising the temperature to reflux such that the reaction is thoroughly performed, to generate the photoresist monomer.

It should be appreciated that the protection gas bubbled in step S4 can be nitrogen to remove other gases in the reactor for maintaining a constant environment for the reaction system. The reaction system is heated to reflux, such as at a temperature of 70-80° C., for 12-26 hr.

It should be understood that the embodiments of the present invention are not limited thereto, and persons skilled in the art can adjust the parts of the starting materials and the solvent as well as the reaction temperature and time of the reaction system according to the disclosure of the present invention and the common knowledge or conventional means in the art, to prepare a photoresist monomer(s), which would be encompassed by the present invention.

The embodiment of the present invention provides a method for preparing a photoresist monomer. $R_3$-substituted benzenesulfonyl chloride-modified polyether polyol and $R_2$-substituted acryloyl chloride structure are incorporated into the photoresist monomer, such that the photoresist monomer can be well cross-linked in oneself or with other components in the photoresist composition via the double-bond group in the subsequent application. Meanwhile, due to the fact that $R_3$-substituted benzenesulfonyl chloride-modified polyether polyol has good compliance and low melting point, the photoresist monomer prepared from it avoids to have high rigidity after baking at a high temperature, increases the gentle degree of angle of slope between film layers, avoids light leak, and improves the performance. Further, the staring materials and solvent used in the preparation method according to the embodiment of the present invention is widely available and inexpensive, and the method is simple and easy to perform, and can be well applied to a production line for mass production.

In step S1, $R_3$-substituted benzenesulfonyl chloride-modified polyether polyol is prepared by polyether polyol as shown by Formula II

II and $R_3$-substituted benzenesulfonyl chloride as shown by Formula III

III

Figure 2:
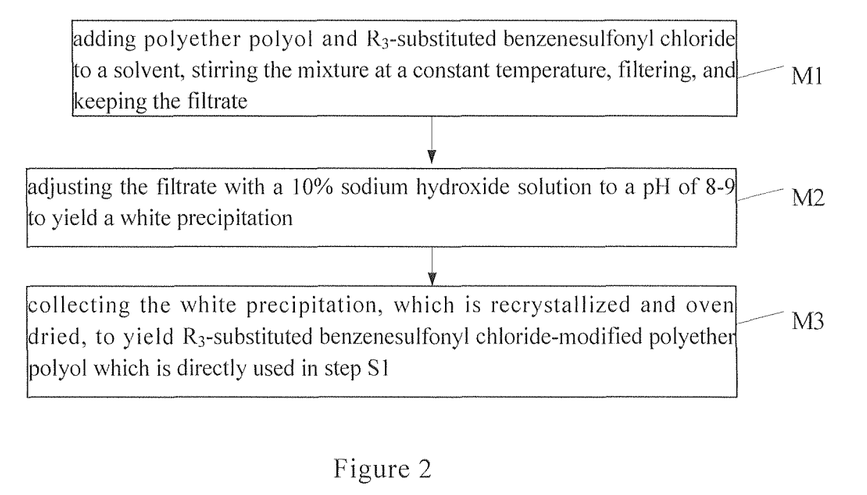
FIG. 2 is a process flow chart of preparing $R_3$-substituted benzenesulfonyl chloride-modified polyether polyol according to an embodiment of the present invention.

For example, as shown by FIG. 2, the procedure comprises:

step M1: adding polyether polyol and $R_3$-substituted benzenesulfonyl chloride to a solvent, stirring the mixture at a constant temperature, filtering, and keeping the filtrate.

In this step, appropriate amounts of polyether polyol, $R_3$-substituted benzenesulfonyl chloride, and solvent are weighted and added to a reaction vessel. For example, polyether polyol used in this step is 2 parts by weight, $R_3$-substituted benzenesulfonyl chloride is 0.7-0.9 part by weight, and the solvent is 100-160 parts by weight.

step M2: adjusting the filtrate with a 10% sodium hydroxide solution to a pH of 8-9 to yield a white precipitation.

step M3: collecting the white precipitation, which is recrystallized and oven dried, to yield $R_3$-substituted benzenesulfonyl chloride-modified polyether polyol which is directly used in step S1.

For example, the solvent for use in recrystallization in step M3 is water, and the recrystallization can be performed for 3 times.

It should be understood that steps M1-M3 represent a preferred embodiment of the present invention where polyether polyol is reacted with $R_3$-substituted benzenesulfonyl chloride to generate $R_3$-substituted benzenesulfonyl chloride-modified polyether polyol. The embodiments of the present invention are not limited thereto and persons skilled in the art can select a specific mode for synthesizing $R_3$-substituted benzenesulfonyl chloride-modified polyether polyol according to the disclosure of the present invention and the common knowledge or conventional means in the art, which would be encompassed by the present invention.

Figure 3:
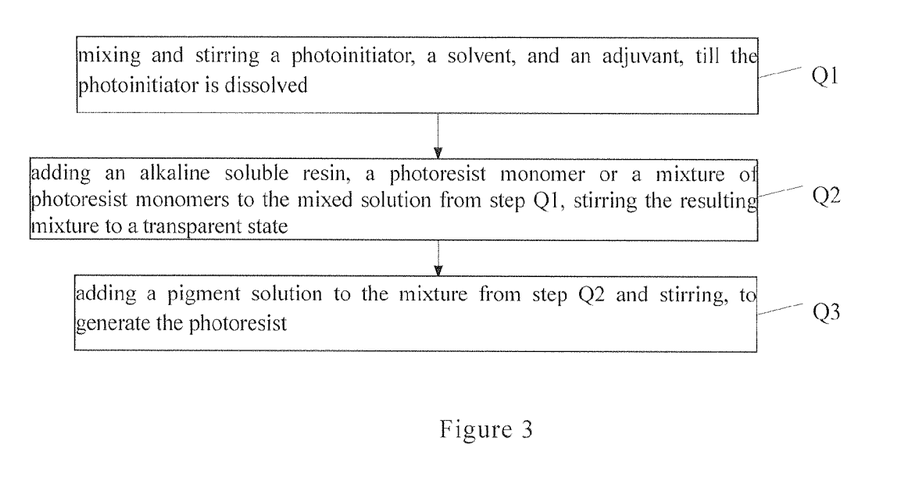
FIG. 3 is a process flow chart of preparing the photoresist according to an embodiment of the present invention.

Corresponding to the photoresist, the embodiment of the present invention further provides a method for preparing the photoresist. As shown in FIG. 3, the method comprises:

step Q1: mixing and stirring a photoinitiator, a solvent, and an adjuvant, till the photoinitiator is dissolved;

step Q2: adding an alkaline soluble resin, a photoresist monomer or a mixture of photoresist monomers to the mixed solution from step Q1, stirring the resulting mixture to a transparent state;

step Q3: adding a pigment solution to the mixture from step Q2 and stirring, to generate the photoresist.

The embodiment of the present invention provides a method for preparing a photoresist. The photoresist is produced by mixing photoresist monomers prepared by a substitution reaction between $R_3$-substituted benzenesulfonyl chloride-modified polyether polyol and $R_2$-substituted acryloyl structure, where the photoresist can be well cross-linked in oneself or with other components in the photoresist composition via the double-bond group in the subsequent application. Meanwhile, due to the fact that $R_3$-substituted benzenesulfonyl chloride-modified polyether polyol in the photoresist has good compliance and low melting point, the photoresist prepared from it avoids to have high rigidity after baking at a high temperature, increases the gentle degree of angle of slope between film layers, and improves the performance. Further, the staring materials and solvent used in the preparation method according to the embodiment of the present invention is widely available and inexpensive, and the method is simple and easy to perform, and can be well applied to a production line for mass production.

Specific examples are provided below for better illustrating the photoresist monomer, the photoresist and the method for preparing the same, color filter according to the present invention. It should be understood that said examples are intended only to illustrate the present invention, not to limit its scope in any way.

Examples 1-4 provide the methods for preparing photoresist monomers A, B, C, and D. Examples 5-7 provide methods for preparing a mixture comprising photoresist monomers A, B, and C, a mixture comprising photoresist monomers A, B, and D, and a mixture comprising photoresist monomers B, C, and D. All components mentioned in the examples are in parts by weight, unless specified otherwise.

Example 1

Preparation of Methyl-Substituted Benzenesulfonyl Chloride-Modified Polyether Triol 2 parts of polyether triol (where, $m_1=60$, $m_2=51$, and $m_3=82$) and 0.9 part of para-methyl benzenesulfonyl chloride are dissolved in 100 parts of acetonitrile and stirred for 2 hr at room temperature. Insoluble material is filtered off, and the filtrate is adjusted to a pH of 8.2 with a 10% sodium hydroxide solution, to yield plenty of white precipitations. The precipitations are filtered, collected, recrystallized in water 3 times, and dried for 12 hr at 50° C. in vacuum, to give methyl-substituted benzenesulfonyl chloride-modified polyether triol.

Methyl-substituted benzenesulfonyl chloride-modified polyether triol is confirmed by a gel permeation chromatography, MW: 8875.

Preparation of Photoresist Monomer A 1 part of methyl-substituted benzenesulfonyl chloride-modified polyether triol as prepared above and 2.3 parts of 2-methyl acryloyl chloride are charged into a three-neck flask, to which 50 parts of tetrahydrofuran is added. 0.015 part of a triethylamine catalyst is added in an ice bath, and the reaction is warmed to 80° C. under nitrogen protection and refluxed for 12 hr. After the reaction is completed, the solid is removed by suction filtration and dried in vacuum, to give the photoresist monomer A.

Photoresist monomer A is confirmed by a gel permeation chromatography, MW: 9009.

The reaction scheme is shown below:

Example 2

Preparation of Ethyl-Substituted Benzenesulfonyl Chloride-Modified Polyether Tetrol Containing a Methyl-Substituted Polyether Chain 2 parts of polyether tetrol containing a methyl-substituted polyether chain (where, $m_1=50$, $m_2=51$, and $m_3=50$) and 0.8 part of para-ethyl benzenesulfonyl chloride are dissolved in 120 parts of acetonitrile and stirred for 2.5 hr at a constant temperature. Insoluble material is filtered off, and the filtrate is adjusted to a pH of 8.4 with a 10% sodium hydroxide solution, to yield plenty of white precipitations. The precipitations are filtered, collected, recrystallized in water 3 times, and dried for 12 hr at 50° C. in vacuum, to give ethyl-substituted benzenesulfonyl chloride-modified polyether tetrol containing a methyl-substituted polyether chain.

Ethyl-substituted benzenesulfonyl chloride-modified polyether tetrol containing a methyl-substituted polyether chain is confirmed by a gel permeation chromatography, MW: 12122.

Preparation of Photoresist Monomer B

1 part of ethyl-substituted benzenesulfonyl chloride-modified polyether tetrol containing a methyl-substituted polyether chain as prepared above and 3.6 parts of 2-ethyl acryloyl chloride are charged into a three-neck flask, to which 45 parts of tetrahydrofuran is added. 0.012 part of a triethylamine catalyst is added in an ice bath, and the reaction is warmed to 80° C. under nitrogen protection and refluxed for 15 hr. After the reaction is completed, the solid is removed by suction filtration and dried in vacuum, to give the photoresist monomer B.

Photoresist monomer B is confirmed by a gel permeation chromatography, MW: 12363.

The reaction scheme is shown below:

-continued

Example 3

Preparation of Propyl-Substituted Benzenesulfonyl Chloride-Modified Polyether Pentol

2 parts of polyether pentol (where, $m_1=62$, $m_2=94$, and $m_3=84$) and 0.7 part of para-propyl benzenesulfonyl chloride are dissolved in 160 parts of acetonitrile and stirred for 4 hr at a constant temperature. Insoluble material is filtered off, and the filtrate is adjusted to a pH of 8.5 with a 10% sodium hydroxide solution, to yield plenty of white precipitations. The precipitations are filtered, collected, recrystallized in water 3 times, and dried for 12 hr at 50° C. in vacuum, to give propyl-substituted benzenesulfonyl chloride-modified polyether pentol.

Propyl-substituted benzenesulfonyl chloride-modified polyether pentol is confirmed by a gel permeation chromatography, MW: 19413.

Preparation of Photoresist Monomer C

1 part of propyl-substituted benzenesulfonyl chloride-modified polyether pentol as prepared above and 4.8 parts of 2-propyl acryloyl chloride are charged into a three-neck flask, to which 80 parts of tetrahydrofuran is added. 0.035 part of a triethylamine catalyst is added in an ice bath, and the reaction is warmed to 80° C. under nitrogen protection and refluxed for 13 hr. After the reaction is completed, the solid is removed by suction filtration and dried in vacuum, to give the photoresist monomer C.

Photoresist monomer C is confirmed by a gel permeation chromatography, MW: 19786.

The reaction scheme is shown below:

Example 4

Preparation of Methyl-Substituted Benzenesulfonyl Chloride-Modified Polyether Hexol

2 parts of polyether hexol (where, $m_1=51$, $m_2=58$, and $m_3=59$) and 0.85 part of para-methyl benzenesulfonyl chloride are dissolved in 100 parts of acetonitrile and stirred for 7 hr at a constant temperature. Insoluble material is filtered off, and the filtrate is adjusted to a pH of 8.6 with a 10% sodium hydroxide solution, to yield plenty of white precipitations. The precipitations are filtered, collected, recrystallized in water 3 times, and dried for 12 hr at 50° C. in vacuum, to give methyl-substituted benzenesulfonyl chloride-modified polyether hexol.

Methyl-substituted benzenesulfonyl chloride-modified polyether hexol is confirmed by a gel permeation chromatography, MW: 15655.

Preparation of Photoresist Monomer D

1 part of methyl-substituted benzenesulfonyl chloride-modified polyether hexol as prepared above and 6.1 parts of acryloyl chloride are charged into a three-neck flask, to which 135 parts of tetrahydrofuran is added. 0.023 part of a triethylamine catalyst is added in an ice bath, and the reaction is warmed to 80° C. under nitrogen protection and refluxed for 14 hr. After the reaction is completed, the solid is removed by suction filtration and dried in vacuum, to give the photoresist monomer D.

Photoresist monomer D is confirmed by a gel permeation chromatography, MW: 15925.

The reaction scheme is shown below:

The photoresist monomers prepared in Examples 1-4 are mixed in a certain ratio to produce the photoresists in Examples 5-7.

Example 5

1.8 parts of a benzophenone photoinitiator (sulphur-containing benzophenone, Kayacure BMS, Nippon Kayaku), 28.5 parts of Propylene glycol monomethyl ether acetate, 0.03 part of a silane coupling agent (g-(methacryloyloxy) propyltrimethoxysilane, Guangzhou Sihai Chemical Business Division), 0.04 part of an antioxidant (tetra[β-(3,5-di-tert-butyl 4-hydroxyphenyl)propanoic]pentaerythritol ester, Zhengzhou Yizhiyuan Chemical Product Co., Ltd.), 0.04 part of an UV absorber (UV-P, Kaiyue Chemical Co., Ltd., Dongguan), 0.03 part of an antifoaming agent (BYK-057, BYK-CHEMIE, Shanghai), 0.02 part of a leveling agent (BYK-356, BYK-CHEMIE, Shanghai) by weight are weighted and mixed together with thorough stirring, till the benzophenone photoinitiator is dissolved. Then, 7.4 parts of amine-modified acrylate (available from Ketian Electronic Material Co., Ltd., Zhongshan), 12.6 parts of a mixture of photoresist monomers (photoresist monomer A, 1 part by weight; photoresist monomer B, 4.3 parts by weight; photoresist monomer C, 5.1 parts by weight) are added and stirred to transparence. 49.3 parts of a pigment dispersion (LCR-1, ENF Technology Co., Ltd., Korean) is added and stirred for more 3 hrs, to product a photoresist.

Example 6

5.8 parts of benzoin photoinitiator (Benzoin bis-methyl ether, Wanduofu Fine Chemical Co., Ltd., Jinan, Shandong), 15.67 parts of propyleneglycol diacetate and ethyl 3-ethoxy-3-imino propionate (volume ratio of propyleneglycol diacetate to ethyl 3-ethoxy-3-imino propionate: 2:1), 0.03 part of a silane coupling agent (γ-mercaptopropyltrimethoxysilane, NANJIN CHUANSHI CHEMICAL CO), 0.02 part of an antioxidant (2,2'-methylenebis(4-methyl-6-tert-butylphenol), NANJIN CHUANSHI CHEMICAL CO), 0.04 part of an UV absorber (UV531, Huaen Chemical Co., Ltd., Shandong), 0.04 part of an antifoaming agent (BYK-141, BYK-CHEMIE, Shanghai), 0.04 part of a leveling agent (BYK-380, BYK-CHEMIE, Shanghai) by weight are weighted and mixed together with thorough stirring, till the benzoin photoinitiator is dissolved. Then, 9.2 parts of polymethacrylate (Pacific Ocean United (Beijing) Petrochemical Co., Ltd), 11.2 parts of a mixture of photoresist monomers (photoresist monomer A, 1 part by weight; photoresist monomer B, 3.5 parts by weight; photoresist monomer D, 3.3 parts by weight) are added and stirred to transparence. 57.6 parts of a pigment dispersion (LCR-1, ENF Technology Co., Ltd., Korean) is added and stirred for 4 hrs, to product a photoresist.

Example 7

11.9 parts of an anthraquinone photoinitiator (2-ethyl anthraquinone, Nanjing Jiean Chemical Co., Ltd.), 11.26 parts of 2-methyl-heptane and cyclohexanone (volume ratio of 2-methyl-heptane to cyclohexanone: 10:1), 0.02 part of a silane coupling agent (2-(3,4-epoxycyclohexyl)ethyltrimethoxysilane, NANJIN CHUANSHI CHEMICAL CO), 0.03 part of an antioxidant (4,4'-sulfbis(6-tert-butyl-3-methylphenol), NANJIN CHUANSHI CHEMICAL CO), 0.03 part of an UV absorber (UV328, Lanzhou Jinwei Group Trade Co., Ltd.), 0.03 part of an antifoaming agent (BYK-070, BYK-CHEMIE, Shanghai), 0.04 part of a leveling agent (BYK-390, BYK-CHEMIE, Shanghai) by weight are weighted and mixed together with thorough stirring, till the anthraquinone photoinitiator is dissolved. Then, 19.8 parts of polymethacrylate (Pacific Ocean United (Beijing) Petrochemical Co., Ltd), 21.2 parts of a mixture of photoresist monomers (photoresist monomer B, 1 part by weight; photoresist monomer C, 2.3 parts by weight; photoresist monomer D, 4.7 parts by weight) are added and stirred to transparence. 35.2 parts of a pigment dispersion (LCR-1, ENF Technology Co., Ltd., Korean) is added and stirred for 4 hrs, to product a photoresist.

Comparative Example 1

1.8 parts of a benzophenone photoinitiator (sulphur-containing benzophenone, Kayacure BMS, Nippon Kayaku), 28.5 parts of propylene glycol monomethyl ether acetate, 0.03 part of a silane coupling agent (g-(methacryloyloxy)propyltrimethoxysilane, Guangzhou Sihai Chemical Business Division), 0.04 part of an antioxidant (tetra[β-(3,5-di-tert-butyl 4-hydroxyphenyl)propanoic]pentaerythritol ester, Zhengzhou Yizhiyuan Chemical Product Co., Ltd.), 0.04 part of an UV absorber (UV-P, Kaiyue Chemical Co., Ltd., Dongguan), 0.03 part of an antifoaming agent (BYK-057, BYK-CHEMIE, Shanghai), 0.02 part of a leveling agent (BYK-356, BYK-CHEMIE, Shanghai) by weight are weighted and mixed together with thorough stirring, till the benzophenone photoinitiator is dissolved. Then, 7.4 parts of amine-modified acrylate (available from Ketian Electronic Material Co., Ltd., Zhongshan), 12.6 parts of a mixture of photoresist monomers (photoresist monomer A, 2 parts by weight; photoresist monomer B, 4.3 parts by weight; photoresist monomer C, 4.1 parts by weight) are added and stirred to transparence. 49.3 parts of a pigment dispersion (LCR-1, ENF Technology Co., Ltd., Korean) is added and stirred for 3 hrs, to product a photoresist.

Comparative Example 2

1.8 parts of a benzophenone photoinitiator (sulphur-containing benzophenone, Kayacure BMS, Nippon Kayaku), 28.5 parts of propylene glycol monomethyl ether acetate, 0.03 part of a silane coupling agent (g-(methacryloyloxy)propyltrimethoxysilane, Guangzhou Sihai Chemical Business Division), 0.04 part of an antioxidant (tetra[β-(3,5-di-tert-butyl 4-hydroxyphenyl)propanoic]pentaerythritol ester, Zhengzhou Yizhiyuan Chemical Product Co., Ltd.), 0.04 part of an UV absorber (UV-P, Kaiyue Chemical Co., Ltd., Dongguan), 0.03 part of an antifoaming agent (BYK-057, BYK-CHEMIE, Shanghai), 0.02 part of a leveling agent (BYK-356, BYK-CHEMIE, Shanghai) by weight are weighted and mixed together with thorough stirring, till the benzophenone photoinitiator is dissolved. Then, 7.4 parts of amine-modified acrylate (available from Ketian Electronic Material Co., Ltd., Zhongshan), 12.6 parts of a mixture of photoresist monomers (photoresist monomer A, 0.1 part by weight; photoresist monomer B, 4.3 parts by weight; photoresist monomer C, 6.0 parts by weight) are added and stirred to transparence. 49.3 parts of a pigment dispersion (LCR-1, ENF Technology Co., Ltd., Korean) is added and stirred for 3 hrs, to product a photoresist.

Performance Testing

Surface and Angle of Scope Investigation

The two photoresists of comparative examples 1-2 and the photoresists of examples 5, 6, and 7 are coated on five glass substrates provided with black matrix and color filter, with a coating thickness of 2.0 μm. Then, the coated substrates are baked for 2-3 min in an oven at 100° C., and irradiated under an UV light at 80-125 mJ/cm². Thereafter, the substrates are developed in a developing solution for 25-40 sec, washed with deionized water, blow-dried, and cured for 30 min in an oven at 230° C.

The glass substrates coated with photoresists are cut at an area of 0.5×0.5 cm², and placed under a scanning electron microscope for testing. Each of the samples is observed for surface appearance and angle of slope. The results are shown in Table 1.

TABLE 1

Surface Appearance and Angle of Slope for Each Sample

| | Comparative Example 1 | Comparative Example 2 | Example 5 | Example 6 | Example 7 |
|---|---|---|---|---|---|
| Surface Appearance | Contracted surface with dark spots | Porous surface | smooth | smooth | smooth |
| Angle of Slope | / | / | 32.8° | 47.6° | 55° |

Figure 4:
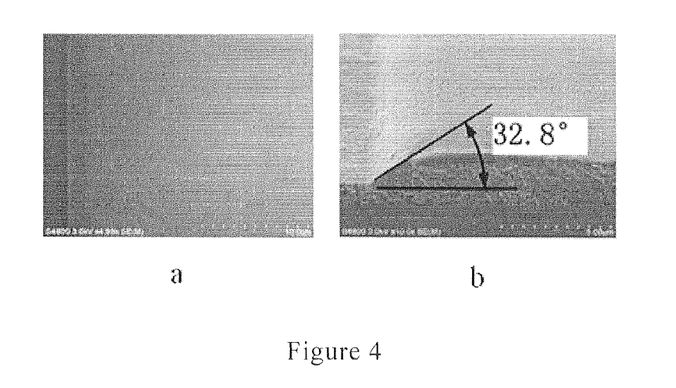
FIG. 4 is a schematic diagram of a surface SEM image and an angle of slope of a photoresist according to an embodiment of the present invention.
Figure 5:
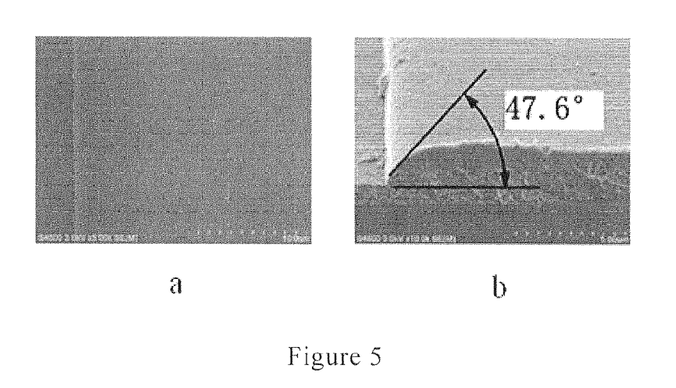
FIG. 5 is a schematic diagram of a surface SEM image and an angle of slope of another photoresist according to an embodiment of the present invention.
Figure 6:
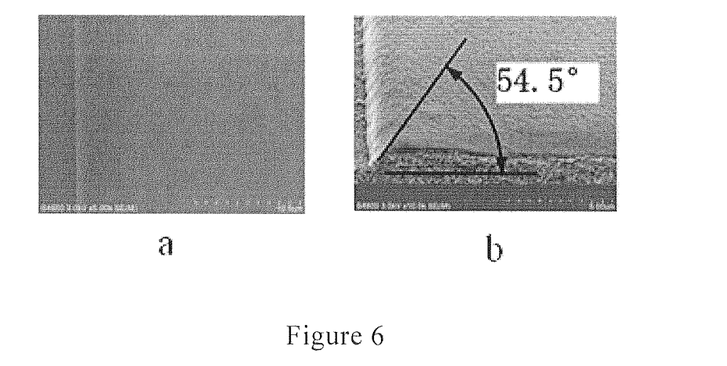
FIG. 6 is a schematic diagram of a surface SEM image and an angle of slope of another photoresist according to an embodiment of the present invention.

As shown in FIGS. 4, 5, and 6, left panels a represent the surface appearance of the photoresists provided in the examples of the present invention after treatment. It can be seen that after the photoresists provided in the examples of the present invention are exposed, the photoresist monomers therein will be cross-linked surrounding via the opening of double-bond functional groups, and the redundant double-bond functional groups will further undergo a sufficient cross-linking reaction with other components in the photoresist, to form a compactly connected network structure, where, the film has a smooth and flat surface. Right panels b represent angles of slope of the photoresists provided in the examples of the present invention after treatment, which are observed under a scanning electron microscope. Since the photoresist according to the embodiments of the present invention contains an aromatic group in its structure, it can increase the compatibility of the monomer with the pigment or other components present in the photoresist system and enhance the film-forming ability of the polyether chain. Further, the incorporation of a sulfonyl group can increase the solubility of the photoresist in the polar solvent and high-temperature heat resistance. Because the polyether structure in the photoresist has good flexibility, low melting point and good solubility, such that the photoresist overcomes the defects that it exhibits high rigidity and is not liable to bend and sink after baking at a high temperature, and the formed angles of slope are quite gentle, being 32.8°, 47.6°, and 55°, respectively, which can satisfy the criterion for angle of slope of greater than 20° and less than 65° in actual production.

Figure 7:
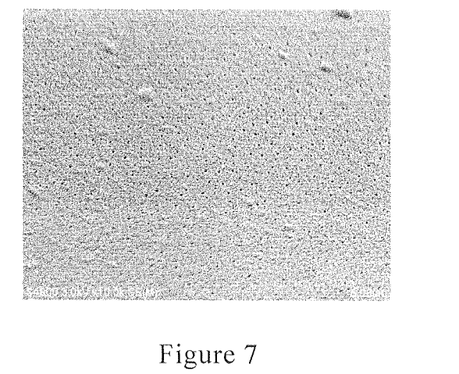
FIG. 7 is a schematic diagram of a surface SEM image of a prior photoresist according to comparative example 1.
Figure 8:
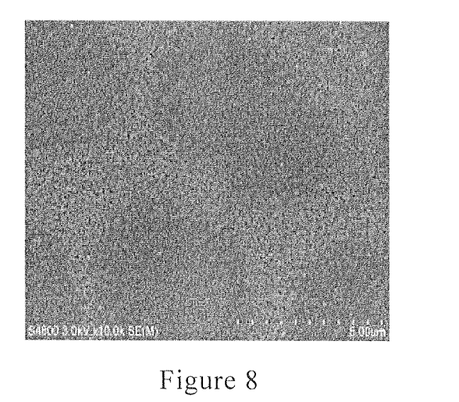
FIG. 8 is a schematic diagram of a surface SEM image of a prior photoresist according to comparative example 2.

FIGS. 7 and 8 show the surface appearances of the treated photoresists from comparative examples 1 and 2 of the prior art, which are observed under a scanning electron microscope. As shown in FIG. 7, in comparative example 1, the amount of low-functionality photoresist monomer (such as, photoresist monomer A) used is quite high, such that the network structure formed after exposure is insufficient in internal cross-linking degree, and the surface of the resulting film appears porous. As shown in FIG. 8, in comparative example 2, the amount of low-functionality photoresist monomer used is extremely low, such that after internal structure is exposed and cured, the photoeresist monomers are further subjected to self-crosslinking during the process of high temperature post-baking, resulting in a film which may be dense somewhere and thin otherwhere, and have a surface being unsmooth and liable to contract.

It can be seen that as compared to the photoresists from the comparative examples, the films formed by the photoresists provided by the examples of the present invention exhibit a smooth surface and gentle angles of slope, due to the incorporation of $R_3$-substituted benzenesulfonyl chloride-modified polyether polyol and $R_2$-substituted acryloyl chloride into the structure as well as the formulation in a proper proportion.

It is apparent that the aforesaid examples are provided for clearly illustrating the present invention, but are not intended to limit the embodiments. Person of ordinary skill in the art can make various modifications or variations based on the above description. It is unnecessary and unable to enumerate all of the embodiments, and thus the obvious modifications or variations derived from these embodiments are also intended to be encompassed by the present invention.

The invention claimed is:

1. A photoresist monomer having a structure represented by Formula I, wherein, $R_1$ is hydrogen or methyl; $R_2$ is hydrogen, methyl, ethyl, or propyl; $R_3$ is hydrogen or $C_{1-6}$ alkyl; and n is from 1 to 4,
wherein, in Formula I, $m_1$, $m_2$, and $m_3$ are in the range of 50-400.

2. A photoresist comprising the photoresist monomer of claim 1, or a mixture of photoresist monomers.

3. The photoresist according to claim 2, wherein, said photoresist further comprises an alkaline soluble resin, a pigment dispersion, a photoinitiator, a solvent, and an adjuvant; said photoresist comprising, in part by weight,
photoresist monomer or a mixture of photoresist monomers: 11.2-21.2 parts;
alkaline soluble resin: 7.4-19.8 parts;
pigment dispersion: 35.2-57.6 parts;
photoinitiator: 1.8-11.9 parts;
solvent: 11.26-28.5 parts; and
adjuvant: 0.07-0.21 part.

4. The photoresist according to claim 3, wherein, the mixture of the photoresist monomers comprises photoresist monomers A, B, and C, wherein,
the photoresist monomer A has a structure of Formula I in which n is 1, and is in 1 part by weight;
the photoresist monomer B has a structure of Formula I in which n is 2, and is in 2.3-4.3 parts by weight; and
the photoresist monomer C has a structure of Formula I in which n is 3, and is in 5.1-5.7 parts by weight.

5. The photoresist according to claim 3, wherein, the mixture of the photoresist monomers comprises photoresist monomers A, B, and D, wherein,
the photoresist monomer A has a structure of Formula I in which n is 1, and is in 1 part by weight;
the photoresist monomer B has a structure of Formula I in which n is 2, and is in 2.7-3.5 parts by weight; and
the photoresist monomer D has a structure of Formula I in which n is 4, and is in 3.3-5.5 parts by weight.

6. The photoresist according to claim 3, wherein, the mixture of the photoresist monomers comprises photoresist monomers B, C, and D, wherein,
the photoresist monomer B has a structure of Formula I in which n is 2, and is in 1 part by weight;
the photoresist monomer C has a structure of Formula I in which n is 3, and is in 2.3-3.1 parts by weight; and
the photoresist monomer D has a structure of Formula I in which n is 4, and is in 4.7-7.5 parts by weight.

7. The photoresist according to claim 2, wherein, the mixture of the photoresist monomers comprises photoresist monomers A, B, and C, wherein,
the photoresist monomer A has a structure of Formula I in which n is 1, and is in 1 part by weight;
the photoresist monomer B has a structure of Formula I in which n is 2, and is in 2.3-4.3 parts by weight; and
the photoresist monomer C has a structure of Formula I in which n is 3, and is in 5.1-5.7 parts by weight.

8. The photoresist according to claim 2, wherein, the mixture of the photoresist monomers comprises photoresist monomers A, B and D, wherein,
the photoresist monomer A has a structure of Formula I in which n is 1, and is n 1 part by weight;
the photoresist monomer B has a structure of Formula I in which n is 2, is 2.7-3.5 parts by weight; and
the photoresist monomer D has a structure of Formula I in which n is 4, and is an 3.3-5.5 parts by weight.

9. The photoresist according to claim 2, wherein, the mixture of the photoresist monomers comprises photoresist monomers B, C, and D, wherein,
the photoresist monomer B has a structure of Formula I in which n is 2, and is in 1 part by weight;
the photoresist monomer C has a structure of Formula I in which n is 3, and is in 2.3-3.1 parts by weight; and
the photoresist monomer D has a structure of Formula I in which n is 4, and is in 4.7-7.5 parts by weight.

10. A color filter, comprising:
a substrate;
a black matrix provided on the substrate; and
a color filter lap-jointly provided on the black matrix, said color filter being formed by the photoresist of claim 2.

11. A method for preparing the photoresist of claim 2, comprising:
Step Q1: mixing a photoinitiator, a solvent, and an adjuvant with stirring, until the photoinitiator is dissolved;
Step Q2: adding a mixture of an alkaline soluble resin, and a photoresist monomer or a mixture of photoresist monomers to the mixed solution from step Q1, and stirring the mixture to a transparent state;
Step Q3: adding a pigment dispersion to the mixture from step Q2, to produce the photoresist.

12. A method for preparing a photoresist monomer is provided, which comprises:
(1) reacting polyether polyol as shown by Formula II with $R_3$-substituted benzenesulfonyl chloride as shown by Formula III

III in a proper solvent, to generate $R_3$-substituted benzene-sulfonyl chloride-modified polyether polyol as shown by Formula IV;

IV (2) reacting $R_3$-substituted benzenesulfonyl chloride-modified polyether polyol as shown by Formula IV with $R_2$-substituted acryloyl chloride as shown by Formula V

V in a proper solvent in the presence of a catalyst, to generate the photoresist monomer having a structure represented by Formula I,

I wherein, $R_1$ is hydrogen or methyl; $R_2$ is hydrogen, methyl, ethyl, or propyl; $R_3$ is hydrogen or $C_{1-6}$ alkyl; and n is from 1 to 4, wherein, in Formula I, $m_1$, $m_2$, and $m_3$ are in the range of 50-400.

13. The method according to claim 12, wherein, polyether polyol, $R_3$-substituted benzenesulfonyl chloride, and the solvent in step (1) are, in parts by weight:

polyether polyol: 2 parts;
$R_3$-substituted benzenesulfonyl chloride: 0.7-0.9 part;
solvent; 100-160 parts.

14. The method according to claim 12,
wherein, $R_3$-substituted benzenesulfonyl chloride-modified polyether polyol, $R_2$-substituted acryloyl chloride, the solvent, and the catalyst in step (2) are, in parts by weight:
$R_3$-substituted benzenesulfonyl chloride-modified polyether polyol: 1 part;
$R_2$-substituted acryloyl chloride: 2.3-6.1 parts;
solvent: 45-135 parts;
catalyst: 0.0145-0.035 part.

* * * * *